United States Patent [19]

Yamashita et al.

[11] 4,008,306

[45] Feb. 15, 1977

[54] METHOD OF RECOVERING MANGANESE VALUES FROM A MIXTURE OBTAINED BY CATALYTICALLY OXIDIZING A PARAFFIN WITH GASEOUS OXYGEN

[75] Inventors: Takashi Yamashita; Tadashi Takeshiro, both of Yokohama, Japan

[73] Assignee: Ajinomoto Co., Inc., Tokyo, Japan

[22] Filed: June 5, 1975

[21] Appl. No.: 584,151

[30] Foreign Application Priority Data

June 14, 1974 Japan .............................. 49-67720
June 14, 1974 Japan .............................. 49-67721

[52] U.S. Cl. .................................. 423/50; 423/51; 423/49; 423/52; 252/413; 260/413; 260/419
[51] Int. Cl.² ........................................ C01G 45/00
[58] Field of Search ................................ 423/49–52; 252/413

[56] References Cited

UNITED STATES PATENTS

| | | |
|---|---|---|
| 3,033,899 | 5/1962 | Knobloch et al. |
| 3,105,851 | 10/1963 | Knobloch et al. |
| 3,780,096 | 12/1973 | Johnson et al. .................. 252/413 |

OTHER PUBLICATIONS

Brennan et al., "Chemical Abstracts", vol. 79, 1973, No. 58180f.
Shibarua et al., "Chemical Abstracts", vol. 80, 1974, No. 17835a.
Kobinat et al., "Chemical Abstracts", vol. 78, 1973, No. 18363r.
Wennerberg et al., "Chemical Abstracts", vol. 79, 1973, No. 70646v.

*Primary Examiner*—Herbert T. Carter
*Attorney, Agent, or Firm*—Hans Berman

[57] ABSTRACT

When paraffins having a chain of 10 – 40 carbon atoms are reacted with gaseous oxygen in the presence of a manganese bearing catalyst, manganese is present in the oxidation mixture partly as a solute in the liquid mixture, and partly as a sludge. When the oxidation mixture is extracted with a dilute mineral acid, practically the entire manganese values present in the mixture are found in the aqueous extract which is free of significant amounts of organic matter. When a more concentrated aqueous acid is used in the extraction, practically the entire manganese values present are converted to a precipitate which is readily recovered and may be dissolved in water for further processing.

5 Claims, No Drawings

METHOD OF RECOVERING MANGANESE VALUES FROM A MIXTURE OBTAINED BY CATALYTICALLY OXIDIZING A PARAFFIN WITH GASEOUS OXYGEN

This invention relates to the separation of fatty acids and other organic materials from a manganese-bearing catalyst employed in producing fatty acids from paraffin, and from manganese-bearing decomposition products of the catalyst. More specifically, the invention relates to a method of recovering manganese values from an oxidation mixture obtained by reacting a paraffin with gaseous oxygen in the presence of a manganese-bearing catalyst to form fatty acids.

When paraffins are oxidized with gaseous oxygen in the presence of a manganese-bearing catalyst until the paraffins are partly converted to monobasic carboxylic acids, the manganese values of the catalyst partly dissolve in the reaction mixture, and partly form a sludge insoluble in water which is suspended in the oxidation mixture and may partly adhere to the walls of the reaction vessel. This occurs regardless of the initial composition of the catalyst, and even if the catalyst was initially soluble in the paraffin employed as a starting material. The catalyst and its manganese-bearing decomposition products must be removed from the oxidation mixture to avoid difficulties during subsequent removal of unsaponifiable matter. Practically complete recovery of the manganese values from the oxidation mixture also is desirable for the economoy of the process.

It was customary heretofore intimately to mix the oxidation product with 10% – 20% water, and to permit the aqueous layer to settle. The manganese values thereby were partly dissolved in the aqueous liquid and partly suspended therein, and the aqueous phase was worked up by neutralizing it with soda ash and separating the manganese-bearing solids from the liquid. Only 50% to 70% of the manganese values present in the oxidation mixture can be recovered in one such operation, and the oxidation mixture must undergo repeated extraction with water for a better yield. The large amounts of water that need to be handled for adequate recovery of manganese values require bulky equipment and relatively much labor.

It has now been found that the manganese values in an oxidation mixture of the type described can be separated practically completely from the organic compounds in the mixture in a single and simple step even when liquid paraffins boiling at 150° to 330° C constitute the starting material and tend to collect much manganese-bearing sludge at the interface of water and organic phase in the conventional method.

According to the invention, the oxidation mixture is intimately mixed with an aqueous solution of a mineral acid. If the acid is dilute, the practically complete manganese values of the catalyst employed are found as solutes in the distinct aqueous layer when separated from the organic phase, and the acidic aqueous phase contains little of the fatty acid which may accompany manganese into the aqueous layer of the conventional method. When the aqueous mineral acid solution is strong or concentrated, a solid phase containing practically the entire manganese values present is formed, and is readily separated from other ingredients of the oxidation mixture which form a liquid, organic phase.

The method of the invention is applicable to all oxidation mixtures conventionally resulting from oxidation of paraffins having 10 to 40 carbons with gaseous oxygen in the presence of a manganese-bearing catalyst. It is presently accepted practice to perform the oxidation at 100° to 140° C, and to blow an oxygen-bearing gas through the liquid paraffin at 100°– 140° C until 20% – 50% of the paraffins originally present is oxidized to carboxylic acids, mainly mono-basic fatty acids. The manganese-bearing catalysts generally employed in this art include manganese salts, particularly those of fatty acids, compounds of manganese with alkali metals, such as potassium permanganate, mixtures of manganese and alkali metal salts of fatty acids, mixed oxides of alkali metals and manganese, such as potassium-bearing manganese dioxide, mixtures of manganese hydroxide and alkali metal salts, and more complex mixtures of manganese compounds with compounds of alkali metals and of other heavy metals such as lead. The transition metals iron and cobalt are frequently associated with the manganese in conventional catalysts. Salts of fatty acids are preferred for obvious reasons when the metals are present in the form of salts. The metals accompanying manganese in the catalyst are also removed from the organic material in the oxidation mixture by the method of this invention. The nature of the manganese moiety in the originally used catalyst is without significant effect on the nature of the manganese-bearing material present after the oxidation of the paraffin, and thus not directly relevant to this invention.

The chemical nature of the acid employed in treating the oxidation mixture by the method according to this invention is unimportant so that the cheapest acids, sulfuric acid, hydrochloric acid, and phosphoric acid are preferred, sulfuric acid being normally superior to the other two in price and imparting convenient properties to the insoluble precipitates formed by treatment of the oxidation mixture with concentrated aqueous mineral acids.

Such precipitates are formed when the mineral acid is applied to the oxidation mixture in a 5-normal or stronger aqueous solution, a 10-normal or stronger acid solution being preferably employed. The upper limit of operativeness is at approximately 36-normal acid, no advantage being achieved by a concentration greater than 20-normal. the particle size of the precipitated manganese compound decreases with increasing acid concentration so that excessive acid concentration may interfere with convenient separation of the precipitate from the liquid present.

The amount of mineral acid to be employed should provide at least the stoichiometric equivalent of the manganese present to form salts of divalent manganese, and may have to be increased in the presence of other metals in the form of their compounds. Generally, the acid provided should preferably be 1.5 to 2.5 times the stoichiometric equivalent of all metals present in the oxidation product, and should not exceed three times the stoichiometric equivalent.

In a widely used process, the catalyst employed amounts to 700 to 1,000 ppm manganese and 500 to 700 ppm alkali metal, based on the weight of the paraffin. Strong sulfuric acid was applied to the oxidation product according to this invention in an amount of 0.3% to 3%, preferably 0.5% to 2.0%, all percentage values herein being by weight unless otherwise specifically indicated. After the reaction and prior to addition of the acid, about 50% to 70% of the manganese values originally supplied was dissolved in the oxidation mixture, the remainder being suspended in the oxidation mixture as a solid sludge or adhering to the reactor walls.

The acid was added to the oxidation mixture in the reactor after the temperature dropped below 100° C, and the contents of the reactor were then stirred for about 10 to 30 minutes to produce a generally crystalline sediment containing the manganese values of the dissolved manganese fraction as well as of the dispersed or adhering sludge. Sometimes 5 minutes are sufficient to cause precipitation, and 60 minutes may be required in other cases. The sediment could readily be recovered by filtration or centrifuging. Not more than 10 ppm manganese could be found in the filtrate or supernatant, nor more of the alkali metal initially present. No less than 99% of the manganese values was thus recovered, and recovery of other metals was at least 98% complete.

The recovered sediment dissolves in water and the manganese ions presented may be precipitated as manganese hydroxide with sodium hydroxide. Manganese hydroxide is an effective catalyst for paraffin oxidation. Only trace amounts of the fatty acids produced by the oxidation could be detected in the manganese sulfate solution.

The remainder of the oxidation mixture, practically free of catalyst, was combined with oily and/or aqueous condensates produced during the oxidation, the combined material was washed with water and further processed in a conventional manner. It did not contain enough manganese to permit quantitative estimation by flame analysis.

When it is desired to recover the manganese values from the oxidation mixture directly as an aqueous solution, the oxidation product is extracted with an aqueous solution about 0.05 to 5-normal with respect to mineral acid, concentrations between 0.1-normal and 3-normal being suitable under most conditions. The amount of acid should be between 0.5 times the stoichiometric equivalent of the metals to be removed and 5 times the stoichiometric equivalent, a range from 1.0 to 2.5 times the stoichiometric equivalent being usually preferred. In the afore-described example of an oxidation product obtained with the use of 700 – 1000 ppm manganese and 500 – 700 ppm alkali metal, the amount of dilute sulfuric acid should be between 2% and 20%, preferably 3% to 15%, of the oxidation product.

The extraction may be carried out batchwise or by continuous countercurrent operation. The residual metal in the oxidate is of the order of a few parts per million, at most a few parts per hundred thousand, while the concentration of each metal in the aqueous extract is between 5,000 and 25,000 ppm. When the extraction is performed batchwise in the reactor employed for the oxidation, sludge adhering to the reactor walls also is removed as a solute. The extract yields manganese hydroxide as described above. The extract contains fatty acids in about the same concentration as in the conventional method, but the weight of the fatty acid is small due to the small volume of aqueous extraction liquid and may be recovered at relatively low cost by known methods.

The extracted oxidate may further be washed with water and is then completely free of metallic moieties of the catalyst.

The following Examples further illustrate the invention.

EXAMPLE 1

A solid paraffin mixture boiling at 340° to 450° C whose carbon distribution curve peaked at $C_{25}$ was oxidized at 110° C with air in the presence of 0.27% potassium permanganate. An oxidation product containing 1000 ppm manganese and 685 ppm potassium was obtained in a yield of 95.1% based on the initial paraffin mixture. A part of the hot oxidation product was filtered, and the filtrate was analyzed for manganese and potassium. 28 Percent of each metal was retained as sludge by the filter, and 72% was found in the filtrate. The oxidation product containing sludge was stirred with 10.2-normal sulfuric acid in a weight ratio of 100 : 0.84 for 20 minutes at 60° C. When stirring was stopped, yellow crystals precipitated at once and were filtered off. The filtrate was found by flame analysis to contain 7.3 ppm Mn and 3.3 ppm K indicating separation efficiencies of 99.3% and 99.5% respectively.

EXAMPLE 2

A liquid paraffin mixture having a distribution peak at $C_{14}$ and a boiling range from 235° to 280° C was oxidized at 120° C with air in the presence of 687 ppm manganese and 442 ppm sodium, and there were obtained an oxidation product containing 770 ppm manganese and 490 ppm sodium, and oily and aqueous condensates which were free from the metals.

1,000 g Oxidation product containing manganese-bearing sludge was stirred with 8.25 g 10-normal sulfuric acid at 60° C for 10 minutes. When the stirring was stopped, faintly yellow crystals precipitated within 2 to 3 minutes. The crystals were filtered off, and the filtrate was subjected to flame analysis. The mangaenese and sodium contents were found to be 0.0 ppm and 5.7 ppm, respectively, corresponding to separation efficiencies of 100.0% and 98.8%.

EXAMPLE 3

1,000 g Oxidation product obtained as in Example 2 was stirred with 8.1 g 15-normal sulfuric acid, and the mixture was further worked up as in Example 2. The manganese and sodium contents in the ultimate filtrate were 0.0 ppm and 9.8 ppm, respectively, which corresponds to separation efficiencies of 100% and 98.0%.

EXAMPLE 4

A liquid paraffin mixture having a distribution peak at $C_{14}$ and a boiling range of 235° to 280° C was oxidized at 120° C with air in the presence of 2,700 ppm manganese, and there were obtained a liquid oxidation product containing 3,400 ppm manganese, and oily and aqueous condensates which were free from the metal. 1,000 g Oxidation product containing sludge was stirred with 9.73 g 19.8-normal sulfuric acid at 50° C for 10 minutes. When the stirring was stopped, faintly yellow crystals precipitated within 2 to 3 minutes. The crystals were filtered off, and the manganese content of the filtrate was found by flame analysis to be 0.05 ppm, which corresponds to a separation efficiency of 99.98%.

EXAMPLE 5

A solid paraffin mixture having a distribution peak at $C_{25}$ and a boiling range from 340° to 450° C was oxidized at 110° C with air in the presence of 0.178% potassium permanganate and 62 ppm potassium hydroxide, and there was obtained an oxidation mixture containing 650 ppm manganese and 530 ppm potassium in a yield of 95% based on the original paraffin mixture.

3,000 g Oxidation mixture containing sludge was stirred with 90 g 1.07-normal sulfuric acid at 60° C for 5 minutes. The mixture was then allowed to stand for 2 hours to separate into an aqueous layer and a clear and colorless oxidate layer. When the two layers were separated in a separatory funnel, only traces a sludges could be observed at the interface.

The aqueous layer weighed 91 g and contained 18,500 ppm Mn and 15,500 ppm K. The oxidate weighed 2,999 g and contained a small amount of suspended sludge giving it a manganese content of 90.0 ppm and a potassium content of 59.9 ppm. Of the combined amount of manganese present in both phases, 86.3% were in the aqueous phase, 13.7% in the oxidate. The corresponding values for potassium were 88.7% and 11.3%.

For comparison purposes, the same procedure was repeated except for the use of 90 g water instead of 1.07-normal sulfuric acid. The weights of the separated aqueous and oxidation layers were the same as above, but the aqueous layer contained only 11,200 ppm (52.0%) Mn and 9,400 ppm (53.5%) K, the oxidate containing the remainder of 312 ppm (48.0%) Mn and 246 ppm (46.5%) K.

EXAMPLE 6

A liquid paraffin mixture having a distribution peak at $C_{14}$ and a boiling range of 235° to 280° C was oxidized at 120° C with air in the presence of 700 ppm manganese and 443 ppm sodium, and there were obtained an oxidation product containing 600 ppm manganese and 380 ppm sodium, and oily and aqueous condensates in respective yields of 85.8, 13.9 and 13.0% by weight based on the paraffin mixture.

8,715 kg Oxidation product was stirred with 84.3 kg 10-normal sulfuric acid and 194 kg water at 50° C for 10 minutes. The mixture was then allowed to stand for 2 hours and to separate into a first aqueous layer A1 and a washed oxidate O1. There was no sludge at the interface, and the layers were easily separated from each other.

The washed oxidate O1 was further stirred with 5% water at 50° C for 10 minutes, and the mixture was again permitted to separate into a second aqueous layer A2 and a twice-washed oxidate O2.

The latter was combined with the oily and aqueous condensates, and then washed with 6,150 kg water. The mixture yielded 10,000 kg of a thrice-washed oxidation product O3 and a third aqueous layer A3.

The several aqueous layers A1, A2, A3 and the three washed oxidates O1, O2, O3 were weighed and analyzed for saponification value, manganese and sodium. The analysis results are tabulated below together with the percent distribution of manganese and sodium between each aqueous layer and the associated washed oxidation product calculated from the analysis data. There is further listed the saponifiable matter (Sap. Matter) present in each aqueous layer and each washed oxidation product in percent of the total saponifiable matter formed by the oxidation of the paraffin. The combined data for aqueous layers A1 and A2 are also listed, and are free of the effects of the condensates on the ultimate composition. The oxidation product which had been washed three times was free from detectable amounts of manganese and sodium, and the combined first and second aqueous layers A1 and A2 contained 99.7% of the manganese values in the original catalyst in readily recoverable form.

TABLE

| Layer or Oxidate | kg | Sap. Matter KOH mg/g | Mn, ppm | Na, ppm | Mn, % | Na, % | Sap. Matter, % |
| --- | --- | --- | --- | --- | --- | --- | --- |
| A1 | 242 | 220.2 | 40,250 | 16,150 | 93.0 | 82.6 | 0.90 |
| A2 | 508 | 93.4 | 1,550 | 1,660 | 6.7 | 16.2 | 2.6 |
| A1 + A2 | 750 | 134.4 | 14,100 | 6,340 | 99.7 | 98.8 | 3.5 |
| A3 | 7,470 | 63.2 | 3.9 | 8.1 | 0.3 | 1.2 | 25.7 |
| O1 | 8,723 | 127.9 | 89 | 22 | 7.0 | 17.4 | 60.7 |
| O2 | 8,621 | 123.9 | 3.4 | 7.0 | 0.26 | 1.2 | 58.1 |
| O3 | 10,000 | 116.2 | 0.0 | 0.0 | 0.0 | 0.0 | 63.2 |

While results analogous to those illustrated in the preceding Examples can be achieved with other mineral acids, the other mineral acids do not present any advantages over sulfuric acid and are more costly. Manganese salts are not readily precipitated from their aqueous solutions by concentrated hydrochloric acid, and it is difficult to solubilize manganese compounds in dilute phosphoric acid. Only sulfuric acid is conveniently employed for transferring manganese values from the liquid organic phase which constitutes the bulk of the oxidation mixture into a distinct phase which may be either liquid and aqueous or solid. Other mineral acids, such as fluoboric acid or hydrobromic acid, which are operative are excluded from further consideration by their cost. However, it may be practical to employ mineral acids other than sulfuric acid under special conditions.

It should be understood, therefore, that the foregoing disclosure relates only to presently preferred embodiments, and that it is intended to cover all changes and modifications of the Examples of the invention herein chosen for the purpose of the disclosure which do not depart from the spirit and scope of the invention set forth in the appended claims.

What is claimed is:

1. A method of recovering manganese values from a liquid oxidation mixture obtained by oxidizing a paraffin having 10 to 40 carbon atoms with gaseous oxygen in the presence of a manganese-bearing catalyst, said mixture essentially consisting of an organic liquid phase containing mono-basic fatty acid produced by said oxidation, unsaponifiable matter, and a portion of said manganese values as a solute, which method comprises:
    (a) contacting said organic liquid phase with aqueous sulfuric acid until said manganese values accumulate substantially completely in a phase distinct from said organic liquid phase;
    (b) separating said organic liquid phase and said distinct phase; and
    (c) recovering manganese values from said distinct phase.

2. A method as set forth in claim 1, wherein said aqueous sulfuric acid is at least 0.05-normal but not more than 5-normal, said aqueous sulfuric acid being contacted with said oxidation mixture in an amount stoichiometrically equivalent to 0.5 to 5 times the amount of metal in said oxidation mixture, said distinct phase being an aqueous liquid.

3. A method as set forth in claim 2, wherein said aqueous sulfuric acid is 0.1 to 3-normal, and said amount is stoichiometrically equivalent to 1.0 to 2.5 times the amount of metal in said oxidation mixture.

4. A method as set forth in claim 1, wherein said aqueous sulfuric acid is 5-normal to 36-normal sulfuric acid, said aqueous sulfuric acid being contacted with said oxidation mixture in an amount stoichiometrically equivalent to 1.0 to 3 times the amount of metal in said oxidation mixture, said distinct phase being solid.

5. A method as set forth in claim 4, wherein said aqueous sulfuric acid is 10-normal to 20-normal, and said amount is stoichiometrically equivalent to 1.5 to 2.5 times the amount of said metal.

* * * * *